United States Patent
Kazuno et al.

(10) Patent No.: US 8,381,336 B2
(45) Date of Patent: Feb. 26, 2013

(54) BED APPARATUS PROVIDED WITH BED-DEPARTURE PREDICTION AND DETECTION SYSTEM

(75) Inventors: Hiroki Kazuno, Tokyo (JP); Hisao Morimura, Tokyo (JP)

(73) Assignee: Paramount Bed Co., Ltd., Tokyo (JP)

( * ) Notice: Subject to any disclaimer, the term of this patent is extended or adjusted under 35 U.S.C. 154(b) by 787 days.

(21) Appl. No.: 12/084,297

(22) PCT Filed: Jan. 19, 2007

(86) PCT No.: PCT/JP2007/050836
§ 371 (c)(1),
(2), (4) Date: Apr. 29, 2008

(87) PCT Pub. No.: WO2007/083767
PCT Pub. Date: Jul. 26, 2007

(65) Prior Publication Data
US 2009/0260158 A1 Oct. 22, 2009

(30) Foreign Application Priority Data

Jan. 20, 2006 (JP) .................................. 2006-012607

(51) Int. Cl.
*G08B 23/00* (2006.01)

(52) U.S. Cl. .............................. 5/600; 5/690; 340/573.4
(58) Field of Classification Search .............. 5/600, 690; 340/573.4
See application file for complete search history.

(56) References Cited

U.S. PATENT DOCUMENTS

| 4,295,133 | A | * | 10/1981 | Vance | 340/573.4 |
| 4,633,237 | A | * | 12/1986 | Tucknott et al. | 340/573.4 |
| 5,276,432 | A | * | 1/1994 | Travis | 340/573.4 |
| 5,479,939 | A | * | 1/1996 | Ogino | 600/595 |

(Continued)

FOREIGN PATENT DOCUMENTS

| JP | 2-280733 | 11/1990 |
| JP | 3093745 | 7/2000 |

(Continued)

OTHER PUBLICATIONS

Barbenel, et al., "Monitoring the mobility of patients in bed", Medical & Biological Engineering & Computing, pp. 466-468 (Sep. 1985).

(Continued)

*Primary Examiner* — William Kelleher
(74) *Attorney, Agent, or Firm* — McGinn IP Law Group, PLLC

(57) ABSTRACT

A load measuring unit detects the load of a bed section and generates a load signal. A body weight computing unit computes the body weight of a user positioned on the bed section on the basis of the load signal. A first determination unit determines whether the body weight is equal to or less than a prescribed threshold. A center-of-gravity position computing unit computes a center-of-gravity position of the user on the basis of the load signal. A second determination unit determines whether the center-of-gravity position is in a monitored area of the bed section. The state of the user is detected to away from the bed when the first determination unit has determined that the body weight is equal to or less than a prescribed threshold, and the second determination unit has determined that the center-of-gravity position is within the monitored area.

7 Claims, 10 Drawing Sheets

U.S. PATENT DOCUMENTS

| | | | |
|---|---|---|---|
| 6,133,837 A * | 10/2000 | Riley | 340/573.1 |
| 6,239,706 B1 * | 5/2001 | Yoshiike et al. | 340/573.4 |
| 6,843,109 B2 * | 1/2005 | Nakada et al. | 73/65.01 |
| 7,253,366 B2 * | 8/2007 | Bhai | 177/45 |
| 7,834,770 B2 * | 11/2010 | Kazuno | 340/573.4 |
| 2003/0090383 A1 | 5/2003 | Conway | |

FOREIGN PATENT DOCUMENTS

| | | |
|---|---|---|
| JP | 2000-325409 | 11/2000 |
| JP | 2001-25490 | 1/2001 |
| JP | 2001-57996 | 3/2001 |
| JP | 3322632 | 6/2002 |
| JP | 2003-52649 | 2/2003 |
| WO | WO 00/51541 | 9/2000 |

OTHER PUBLICATIONS

Japanese Office Action dated Feb. 9, 2010 with partial English translation.

European Search Report dated May 20, 2011.

* cited by examiner

BED APPARATUS PROVIDED WITH BED-DEPARTURE PREDICTION AND DETECTION SYSTEM

TECHNICAL FIELD

The present invention relates to a bed apparatus provided with a bed-departure prediction and detection system for determining bed-departure/bed-presence of elderly persons suffering from dementia, patients that have recently undergone surgery, or other persons, and for predicting bed-departure from the movement of a user on the bed.

BACKGROUND ART

In recent years, wandering of elderly persons suffering from dementia and accidents involving stumbling and falling in the vicinity of the bed have become a social problem, and a solution to this problem is needed. There are high expectations that a quicker response can be achieved during an abnormal situation by monitoring the on-bed movements of elderly person, patients that have recently undergone surgery, or other users who are bedridden over a long period of time, by using the load information of the bed.

The art disclosed in patents document 1 merely uses weight information to determine whether a user is still on the bed or has left the bed, and cannot monitor the movement of the user on the bed.

The arts disclosed in patent documents 2 to 4 and non-patent document 1 solve this problem by calculating the center of gravity from the weight information of four points on the bed, and use the center-of-gravity position information to monitor the movement of a user in bed.

Patent Document 1: Japanese Laid-Open Patent Application No. 2-280733
Patent Document 2: Japanese Patent No. 3093745
Patent Document 3: Japanese Patent No. 3322632
Patent Document 4: U.S. Pat. No. 5,276,432
Non-patent Document 1: J. C. Barbenel et al., Monitoring the mobility of patients in bed, Medical & Biological Engineering & Computing, pp. 466-468 (September 1985)

DISCLOSURE OF THE INVENTION

Problems the Invention is Intended to Solve

However, in patent documents 2 to 4, even though the user can be determined to be at the edge of the bed, for example, by monitoring only information related to the center-of-gravity position of the user on the bed, it cannot be determined whether the user is at the edge of the bed due to turning over in bed or moving in another manner, whether the user is at the edge of the bed in an attempt to leave the bed, or whether the variations in the center-of-gravity position are due to an item being placed on the bed section in which the user is lying down, or another non-user person leaning or sitting on the bed section. Also, there is a problem in that distinction cannot be made from a sit-up movement, and errant determinations may occur when the center of gravity has changed due to the railing or other accessory items being removed.

The art disclosed in non-patent document 1 is one in which the load of four bed legs is measured by load cells, and the body weight of a patient on a bed is measured in order to monitor the movement of the patient on the bed. The center of gravity on the bed is computed from the difference in the load measurement values of the bed legs, and the movement distance of the center of gravity is computed. Also disclosed is an art in which the state of the patient is determined from the number of movements of the patient on the bed.

However, in the art disclosed in non-patent document 1, there is a problem in that the movement of the user on the bed cannot be determined to be movement of the center of gravity that is caused by an item being placed on the bed section in which the user is sleeping, or another non-user person leaning or sitting on the bed section, because the movement of the user on the bed is measured by using only the movement distance of the center of gravity on the bed, and such a situation leads to errant determinations.

An object of the present invention is to provide a bed apparatus provided with a bed-departure prediction and detection system in which the movement of a user can be more accurately monitored by determining information that includes a combination of the body weight information and center-of-gravity position information of the user, and in which the movement of a user can be monitored with high reliability, few detection errors, and high detection accuracy.

Means for Solving the Problems

The bed apparatus according to a first aspect of the present invention comprises a load measuring unit for detecting the load of a bed section and generating a load signal; a body weight computing unit for computing the body weight of a user positioned on the bed section on the basis of the load signal; a first determination unit for determining whether the body weight is equal to or less than a prescribed threshold; a center-of-gravity position computing unit for computing a center-of-gravity position of the user on the basis of the load signal; and a second determination unit for determining whether the center-of-gravity position is in a monitored area of the bed section, wherein the state of the user is detected when the first determination unit has determined that the body weight is equal to or less than a prescribed threshold, and the second determination unit has determined that the center-of-gravity position is within the monitored area.

The user is in a side-sitting position when the monitored area is, e.g., the side-sitting position of a bed section.

When the user sits in the side-sitting position of the bed section and lowers his feet to the floor, the load detection value detected by the load measuring unit is reduced and the body weight computed by the body weight computing unit is reduced. In view of the above, the user can be detected to be in a side-sitting position when the first determination unit has determined that the body weight is equal to or less than a prescribed threshold and when the second determination unit has determined that the center-of-gravity position of the user is a side-sitting position.

The bed apparatus preferably has a body weight threshold setting means for setting the threshold of the body weight, and a center-of-gravity position monitored area setting unit for setting the monitored area of the center-of-gravity position.

The bed apparatus may also have an alarm unit for generating an alarm when the state of the user has been detected.

The bed apparatus may also have a bed height storage unit for storing a bed section height reference value; and a bed height determination unit for determining whether the current bed section height is greater than the bed section height reference value, wherein the state of the user is detected solely by the determination result of the second determination unit regardless of the determination result of the first determination unit when the bed height determination unit has determined that the current bed section height is greater than the bed section height reference value.

The bed apparatus may also be provided with a user body information input unit for inputting body information of the user, and a center-of-gravity position monitored area setting unit for setting the optimal center-of-gravity position monitored area, based on the inputted user body information.

The bed apparatus may also be provided with a center-of-gravity position monitored area setting unit for setting the optimal center-of-gravity position monitored area, based on the center-of-gravity position of the user computed by the center-of-gravity position computing unit.

The bed apparatus according to another aspect of the present invention comprises a load measuring unit for detecting the load of a bed section and generating a load signal; a body weight computing unit for computing the body weight of a user positioned on the bed section on the basis of the load signal; a first determination unit for determining whether the body weight is equal to or less than a prescribed threshold; a center-of-gravity position computing unit for computing a center-of-gravity position of the user on the basis of the load signal; a center-of-gravity movement distance computing unit for computing the movement distance of a center-of-gravity position from the result of computing the center-of-gravity position; and a second determination unit for determining whether the movement distance of the center-of-gravity position has exceeded a second threshold, wherein the state of the user is detected when the second determination unit has determined that the movement distance of the center-of-gravity position has exceeded the second threshold, and the first determination unit has determined that the body weight is equal to or less than the first threshold.

The bed apparatus may also detect a sitting-up action of the user when, e.g., the threshold of the movement distance of the center-of-gravity position is set based on the movement distance of the center-of-gravity position when the user has sat up.

The center of gravity of the user moves from the head side to the foot side in the lengthwise direction of the bed section when the user makes a sitting-up movement on the bed. It is preferably determined whether movement of the center-of-gravity position is due to a sitting-up action by the user, is due to the placement of an article on the bed section, is due to another person who is not the user leaning on the bed section, or is due to another cause, when the second determination unit has determined that the movement distance of the center-of-gravity position in the lengthwise direction of the bed section has exceeded the second threshold. Therefore, the user can be detected to have made a sitting-up action when the second determination unit has determined that the movement distance of the center-of-gravity position in the lengthwise direction of the bed section has exceeded the second threshold, and the first determination unit has determined that the body weight is equal to or less than the first threshold.

The bed apparatus preferably detects the state of the user when the first determination unit has furthermore determined whether the body weight is within a prescribed range, the second determination unit has determined that the movement distance of the center-of-gravity position has exceeded the second threshold, and the first determination unit has determined that the body weight is equal to or less than the first threshold and is within a prescribed range.

The bed apparatus has a body weight threshold setting unit for setting the first threshold, a center-of-gravity position movement distance threshold setting unit for setting the second threshold of the center-of-gravity position, a body weight range setting unit for setting a prescribed range of the body weight, and a center-of-gravity movement distance time difference setting unit for setting the time difference between two time instances that are used to compute the movement distance of the center-of-gravity position.

The bed apparatus can have an alarm unit for generating an alarm when a sitting-up movement of the user is detected.

Another aspect of the bed apparatus of the present invention has a load measuring unit for detecting the load of a bed section and generating a load signal; a body weight computing unit for computing the body weight of a user positioned on the bed section on the basis of the load signal; an abnormality detection unit for determining that the body weight in not within a prescribed range and detecting an abnormality; and a body weight monitoring unit for monitoring the time the body weight has not been within the prescribed range, wherein a weight abnormality is detected when the body weight monitoring unit has detected that the state in which the body weight is not within the prescribed range has continued for a prescribed length of time.

Accurate detection may be prevented because the load detection value of the load measuring unit varies and the body weight computed by the body weight computing unit varies when a bed cover, railing, or other accessory item is removed from or added to the bed section. In view of this situation, the abnormal detection unit determines that the body weight is outside of a prescribed range and detects an abnormality, and a weight abnormality is detected when the body weight monitoring unit detects that the state in which the body weight is outside of the prescribe range has continued for a prescribed length of time.

The bed apparatus preferably has a body weight range setting unit for setting a prescribed range of the body weight, and a body weight-monitoring time setting unit for setting the time for monitoring the body weight computing value.

The bed apparatus can have an alarm unit for generating an alarm in accordance with body weight abnormal detection.

Another aspect of the bed apparatus of the present invention has a load measuring unit for detecting the load of a bed section and generating a load signal; a body weight computing unit for computing the body weight of a user positioned on the bed section on the basis of the load signal; a first determination unit for determining whether the body weight is equal to or greater than a prescribed threshold; a center-of-gravity position computing unit for computing a center-of-gravity position of the user on the basis of the load signal; a second determination unit for determining whether the center-of-gravity position is in a monitored area of the bed section; and a body weight center-of-gravity position monitoring unit for monitoring the time in which the body weight is equal to or greater than a prescribed threshold and in which the center-of-gravity position is in the monitored area, wherein the state of the user is detected when the body weight center-of-gravity position monitoring unit has detected that the body weight is equal to or greater than a prescribed threshold and that a state in which the center-of-gravity position is in the monitored area has continued for a prescribed length of time.

The state of the user is an abnormal state when the monitored area is, e.g., in an unnatural position for the center of gravity of the user to be on the bed section.

A possible state in which the user remains in an unnatural position on the bed section is one in which the body of the user is on the bed section, or only a portion of the body of the user is on the bed section. In order to eliminate the latter state, the first determination unit determines that the body weight is equal to or greater than a prescribed threshold, and a second detection unit detects that the center-of-gravity position of the user is an abnormal position. The state of the user is detected to be one in which the user is in an abnormal position when the body weight center-of-gravity position monitoring unit has detected that the body weight is equal to or greater than a prescribed threshold and that the center-of-gravity position of the user has continued for a prescribed length of time to be in a state of being in an abnormal position.

The bed apparatus preferably has a body weight threshold setting unit for setting the threshold of the body weight, a center-of-gravity position monitored area setting unit for setting the monitored area of the center-of-gravity position, and body weight center-of-gravity position monitoring time setting unit for setting the body weight center-of-gravity position monitoring time in which the body weight is equal to or greater than a prescribed threshold and in which the center-of-gravity position is in the monitored area.

The bed apparatus may have an alarm unit for generating an alarm in accordance with abnormal position detection.

The bed apparatus according to the present invention preferably has a body weight threshold setting unit for setting the optimal body weight threshold, based on the computed value of the body weight of the user.

The bed apparatus may have an alarm unit for generating an alarm in accordance with a determination result that corresponds to the body weight threshold set by the body weight threshold setting unit.

The bed apparatus according to the present invention may have a user health condition information input unit for inputting health condition information of a user, and an alarm setting unit for setting the optimal alarm unit, based on the inputted user health condition information.

The bed apparatus may also have a related-threshold setting unit that is capable of setting a threshold related to the alarm unit selected by the alarm setting unit, based on the health condition of the user and the body information of the user.

Effect of the Invention

In accordance with the present invention, the combined information of the body weight information and center-of-gravity position information of the user is determined, whereby the movement of the user can be more accurately monitored. False alarms of bed departure detection can be reduced and system reliability is improved even under conditions in which such information cannot be determined in the prior arts.

| | [Key] |
|---|---|
| 1: | bed section |
| 2: | frame |
| 3: | load sensor |
| 3-1: | first load sensor |
| 3-2: | second load sensor |
| 3-3: | third load sensor |
| 3-4: | fourth load sensor |
| 4: | wall section |
| 5: | bed-departure prediction and detection system controller |
| 6: | side-sitting position detection area |
| 20: | controller |
| 21: | computing unit |
| 22: | storage unit |
| 23: | operation and display unit |
| 24: | setting and operation unit |
| 25: | alarm display unit |
| 26: | alarm/stop operation unit |
| 28: | personal computer |
| 29: | nurse call signal |
| 30: | nurse station |
| 31: | alarm signal generator |

BEST MODE FOR CARRYING OUT THE INVENTION

Figure 1:
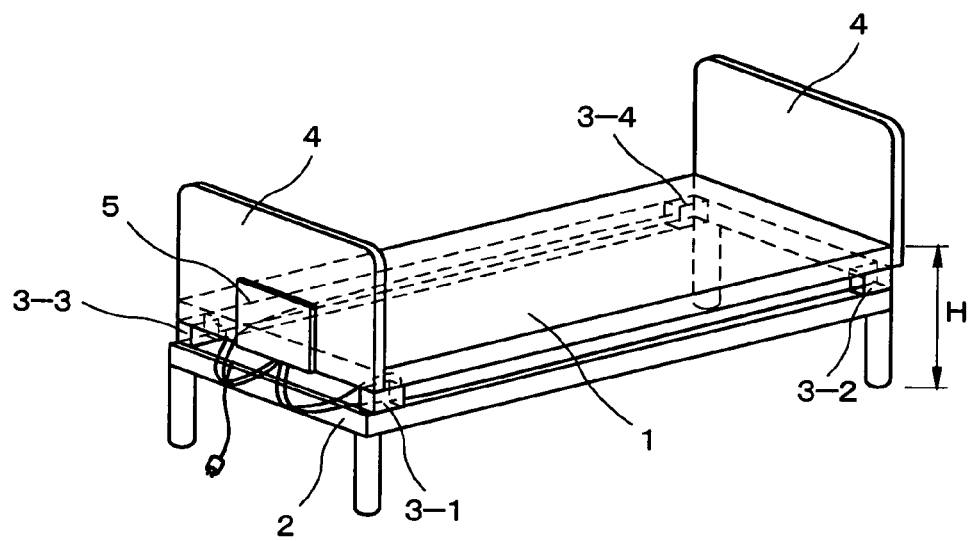
FIG. 1 is a schematic view of the bed apparatus according to embodiment 1 of the present invention.

The bed apparatus according to embodiments of the present invention is described in detail below with reference to the attached diagrams. The bed apparatus of embodiment 1 provided with a side-sitting position detection function will be described first. The side-sitting position detection function is a function for detecting that a patient (user) on a bed is in a state of sitting at the edge of the bed and is attempting leave the bed. FIG. 1 is a schematic view of the bed apparatus according to embodiment 1 of the present invention. Four load sensors 3 for detecting the load on the bed section 1 and generating a load signal are provided to the four corners of a legged frame 2 that supports the bed section 1. The load signals generated by the load sensors 3 are read at fixed time intervals by a bed-departure prediction and detection system controller 5 (hereinafter referred to as "controller 5") provided to one of the wall sections 4 that are disposed on the two short sides of the bed section 1.

The controller 5 is provided with a body weight computing unit, a center-of-gravity position computing unit, a first determination unit, a second determination unit, a body weight threshold determination unit, a center-of-gravity position monitored area setting unit, a storage unit, an alarm apparatus, an alarm selection unit, and the like. Detection performed by each unit is carried out by software. The controller 5 reads load signals generated by the load sensors 3 at fixed time intervals. The body weight computing unit computes the body weight of the user on the bed section 1 on the basis of the signal thus read. Since a mattress, bed cover, railing, and other accessory items (not shown) are provided to the bed section 1, the body weight computing unit uses this state as a reference point (=0 kg, origin correction of the center-of-gravity position), reads the load signals of the bed section 1 using the controller 5 when the user is lying on the bed section 1, and computes the body weight $W_T$ of the user by computing the load increase from the reference point.

Figure 2:
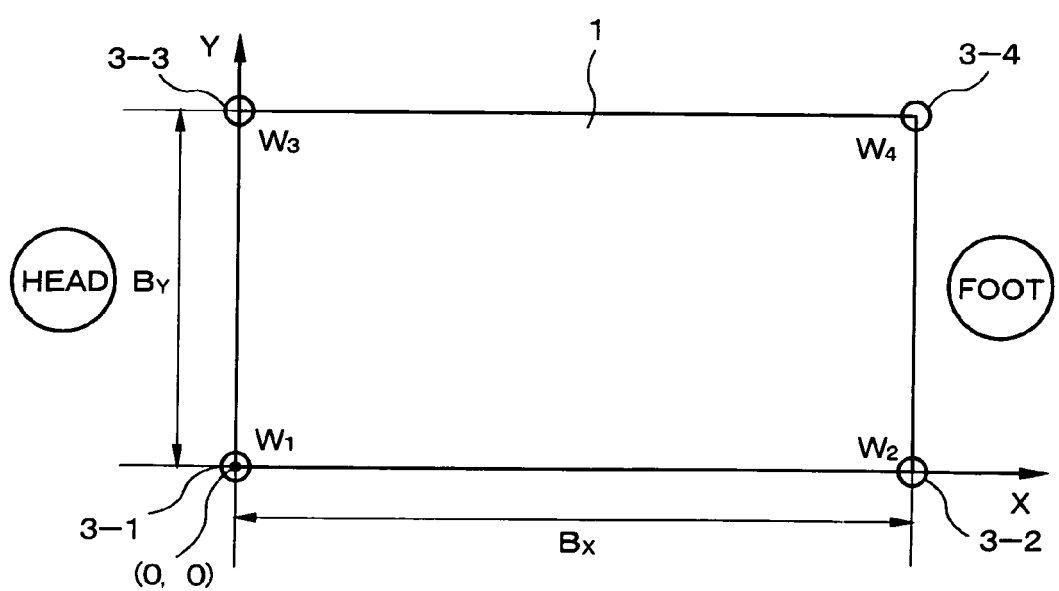
FIG. 2 is a schematic diagram showing an example in which four load sensors 3-1 to 3-4 are disposed at the four ends of the bed section 1.

The center-of-gravity position computing unit computes the center-of-gravity position of the user on the bed section 1 on the basis of the load signals generated by the load sensors 3 that are read by the controller 5 at fixed intervals. FIG. 2 is a schematic diagram showing an example in which four load sensors 3-1 to 3-4 are disposed at the four ends of the bed section 1. The head side is the side that connects the first load sensor 3-1 and the third load sensor 3-3, and the foot side is the side that connects the second load sensor 3-2 and the fourth load sensor 3-4. The origin (0, 0) is the left end of the head side (lower left end section of the bed section 1 in FIG. 2) of the bed section 1, $B_X$ is the distance between the first load sensor 3-1 and the second load sensor 3-2, and $B_Y$ is the distance between the first load sensor 3-1 and the third load sensor 3-3. The center-of-gravity position (X, Y) of the user can be expressed by the following formula 1, wherein $W_1$ to $W_4$ ($W_1+W_2+W_3+W_4=W_T$) are the calculated values of the load increase from the reference values of the load signals generated by the first to fourth load sensors 3-1 to 3-4 when the user is lying on the bed section 1. In accordance with this formula, the center-of-gravity position computing unit computes the center-of-gravity position of the user on the bed section 1.

$$(X, Y) = \left( \frac{(W_2 + W_4) \cdot B_X}{W_T}, \frac{(W_3 + W_4) \cdot B_Y}{W_T} \right) \quad [\text{EQ. 1}]$$

The first determination unit monitors the body weight $W_T$ of the user on the bed section 1 computed by the body weight computing unit, and determines whether the body weight $W_T$ of the user is equal to or less than a prescribed body weight threshold $W_{T1}$. The second determination unit monitors the center-of-gravity position $(X_1, Y_1)$ of the user and determines whether the center-of-gravity position $(X_1, Y_1)$ of the user is in the center-of-gravity position monitored area of the bed section 1. The center-of-gravity position monitoring area is the edge of the bed, i.e., the side-sitting position. Therefore, the center-of-gravity position monitor area may be all four edges surrounding the bed, or may be an area of a portion of the edges. Also, the center-of-gravity position monitored area is not necessarily limited to the side of the bed, and the monitor area is set depending on the purpose of monitoring the state of the patient.

The body weight threshold setting unit sets the body weight threshold $W_{T1}$ when it is determined whether the user on the bed section 1 is sitting on the edge of the bed. The center-of-gravity position monitored area setting unit uses the center-of-gravity position monitor area as the side-sitting position and sets an area of the edge section (side-sitting position) of the bed when the side-sitting position of the user on the bed section 1 is to be detected. The body weight threshold $W_{T1}$ and the side-sitting position detection area are inputted from a personal computer connected to the controller 5, are computed in the computing unit of the controller 5, and are stored in the storage unit.

The alarm apparatus generates an alarm in accordance with the determination results of the first determination unit and the second determination unit. The alarm selection unit has a function for selecting the existence and type of alarm.

Figure 3:
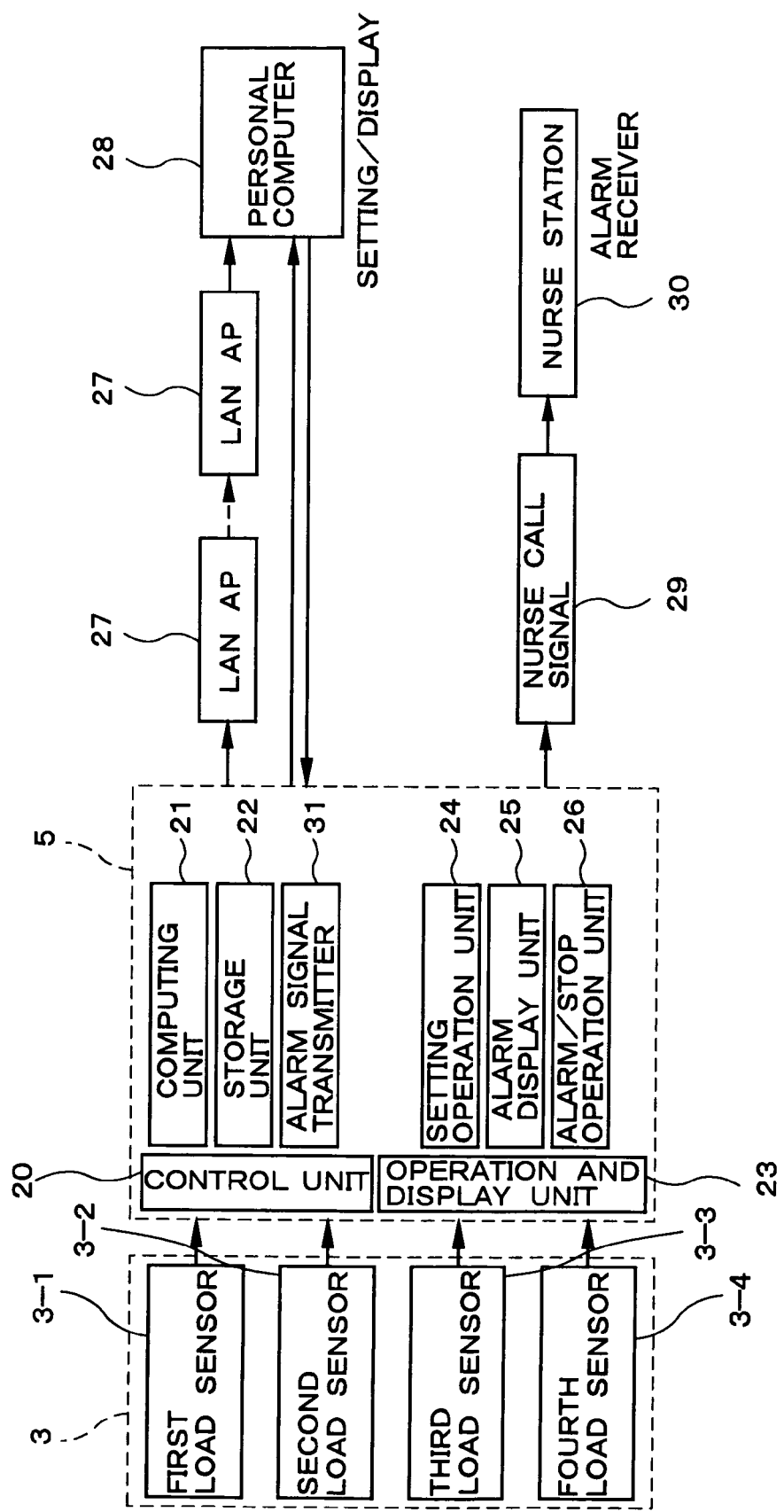
FIG. 3 shows a block diagram of when signals of the load sensors 3 are processed as information by a controller 5 and the functions are operated.

FIG. 3 shows a block diagram of when signals of the first load sensor 3-1 to fourth load sensor 3-4 are processed as information by the controller 5, and the functions are operated. The load signals generated by the first to fourth load sensors 3-1 to 3-4 are read and computed by the computing unit 21 of the encoder 5 at fixed intervals. The computing unit 21 has a body weight computing unit for computing the body weight $W_T$ of a user on the bed section 1, a center-of-gravity position computing unit for computing the center-of-gravity position of the user on the bed section 1, a first determination unit for determining whether the body weight of the user is equal to or less than a prescribed body weight threshold $W_{T1}$, and a second determination unit for monitoring the center-of-gravity position $(X_1, Y_1)$ of the user and determining whether the center-of-gravity position $(X_1, Y_1)$ of the user is in the center-of-gravity position monitored area of the bed section 1, and also has a storage unit 22 for storing the body weight threshold, the center-of-gravity position monitored area, and the like that are used for making the first and second determinations, and an alarm signal generator 31 for generating an alarm by using the determination result of the first determination unit and the second determination unit. The controller 5 has an operation switch, a setting and operation unit 24 such as a power switch, an alarm display unit 25, a nurse call signal 29, and other alarm/stop operation units 26.

An alarm apparatus generates an alarm signal via the controller 5, and a nurse station 30 can be notified via the nurse call signal 29, or a remote personal computer 30 may be notified by relay through a LAN (Local Area Network) access point 27 by using a communication connector 12 when a plurality of beds is being managed.

Next, the operation of the bed-departure prediction and detection system according to embodiment 1 of the present invention configured in the manner described above will be described. Since a mattress, bed cover, railing, and other accessory items (not shown) are provided to the bed section 1, the body weight computing unit uses this state as a reference point (=0 kg, origin correction of the center-of-gravity position), reads the load signals of the bed section 1 using the controller 5 when the user is lying on the bed section 1, and computes the body weight $W_T$ of the user by computing the load increase from the reference point. An operation switch of the controller 5 (not shown) is pressed or a personal computer is operated immediately after the user has lain on the bed section 1, whereby the body weight of the user can be stored in the storage unit 22 of the controller 5. The body weight of the user at this time is set as the reference body weight $W_S$. The reference body weight $W_S$ of the user can also be stored in the storage unit of the controller 5 by inputting the body weight of the user that has been obtained using a weight scale or the like, and inputting the result via a personal computer connected to the controller 5.

Figure 4:
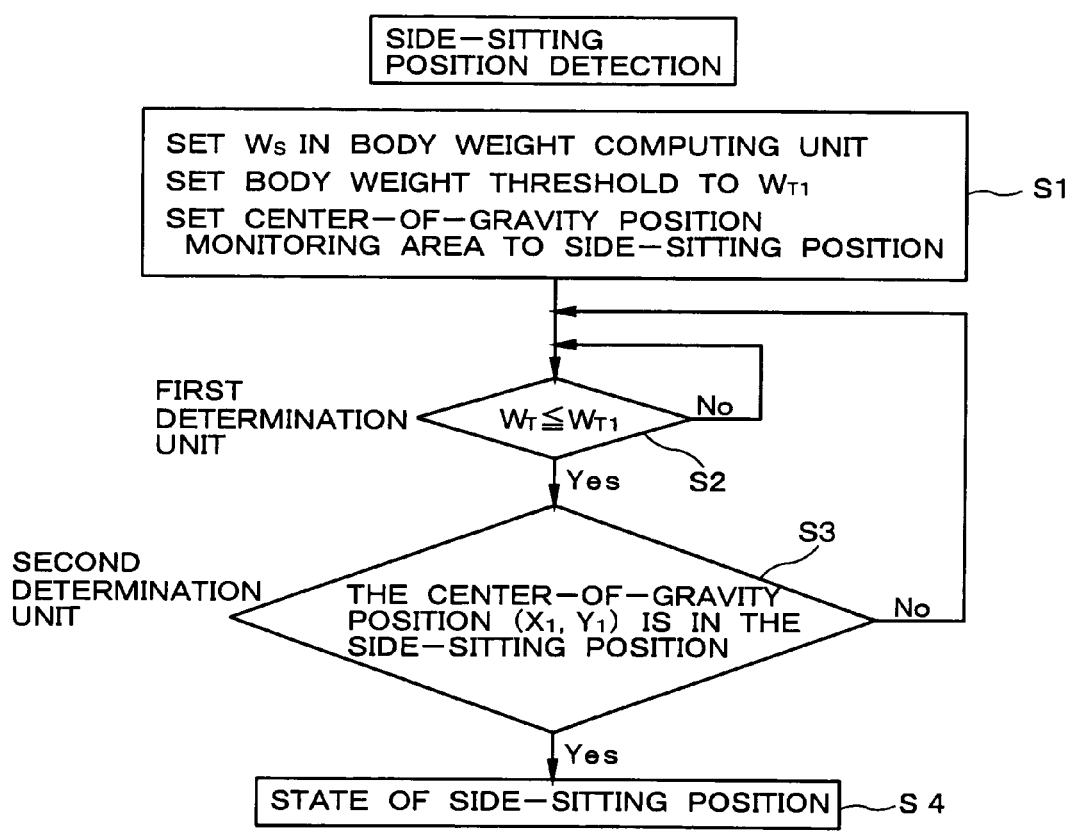
FIG. 4 is a diagram showing the flow of side-sitting position detection.

FIG. 4 is a flowchart showing the flow of side-sitting position detection. The reference body weight $W_S$ of the user on the bed section 1 is computed by the body weight computing unit of the computing unit 21 of the controller 5 in advance when a reference is obtained, the body weight threshold $W_{T1}$ is set by the body weight threshold setting unit, the side-sitting position is set by the center-of-gravity position monitored area setting unit, and these values are stored in the storage unit 22 of the controller 5 (step 1).

When the user is in a side-sitting position, i.e., when the user has moved to the edge section of the bed and is in a sitting state, the center-of-gravity position is in the center-of-gravity position monitored area, and the load detection value of the load measuring unit is reduced when the user's feet make contact with the floor and the body weight $W_T$ of the user computed by the body weight computing unit is reduced. In view of this situation, in the present embodiment, the first determination unit detects a reduction in the body weight $W_T$ of the user in addition to the second determination unit detecting whether the center-of-gravity position of the user is in the side-sitting position. It is known that the user is at the edge section of the bed section 1 even when the user moves to the edge section position of the bed, but it cannot be known if the state is one in which the center-of-gravity position is at the edge section of the bed section 1 due to turning over in bed or another action, or if the state is one in which the user is actually in the side-sitting position. For this reason, the load detection value of the load measuring unit, which is reduced when the user's feet make contact with the floor, and the reduced body weight $W_T$ of the user computed by the body weight computing unit are determined in combination, whereby false alarms can be reduced in terms of detecting a side-sitting position.

In other words, the body weight $W_T$ of the user on the bed section 1 that is computed by the body weight computing unit is monitored, and the first determination unit determines (step 2) that the body weight $W_T$ of the user is equal to or less than the body weight threshold $W_{T1}$ when the body weight $W_T$ of the user is equal to or less than the body weight threshold $W_{T1}$ (e.g., 75% of the reference body weight $W_S$ of the user).

The second determination unit determines that the center-of-gravity position of the user is in the edge section of the bed (side-sitting position) when the center-of-gravity position $(X_1, Y_1)$ of the user is in the side-sitting position detection area of the bed section 1 (step 3).

The user is detected to be in a side-sitting position state when the first determination unit has determined that the body weight $W_T$ of the user is equal to or less than the body weight threshold $W_{T1}$, and the second determination unit has determined that the center-of-gravity position of the user is in the side-sitting position (step 4).

As described above, the center-of-gravity position is determined to be in the side-sitting position during side-sitting position detection. A determination is also added wherein, as a result of the fact that the user's feet make contact with the floor, the load detection value of the load measuring unit is reduced, as is the body weight $W_T$ of the user computed by the body weight computing unit, whereby it can be known if the state is one in which the user is at the edge section of the bed due to turning over in bed or another action, or if the state is one in which the user is in a side-sitting position in an attempt to leave the bed, and false alarms can be reduced with respect to side-sitting position detection. An alarm can be actuated when the user has been detected to be in a side-sitting position in an attempt to leave the bed.

The alarm apparatus generates an alarm depending on the result of detecting the side-sitting position, and the alarm selection unit has a function for selecting the existence of an alarm and the type of alarm. When an alarm is being generated, a nurse is notified by way of a nurse call signal 29, or a personal computer 28 or the like, and notification can be made using an alarm display unit 25 of the controller 5.

Figure 5:
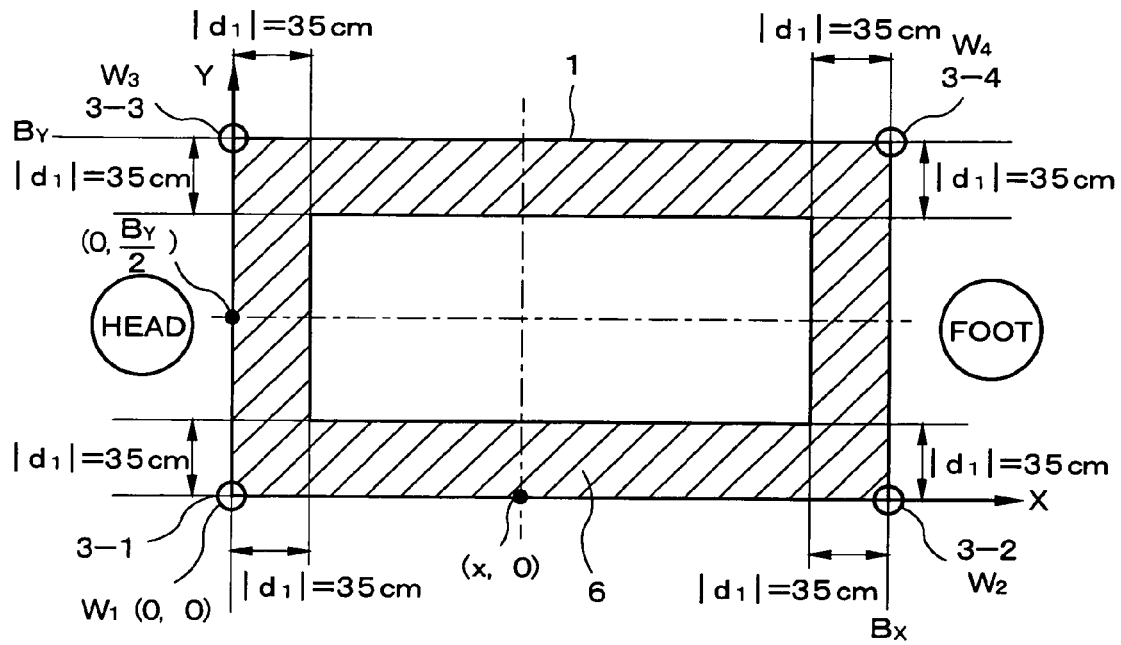
FIG. 5 is a diagram showing an example of the side-sitting detection area 6 of a bed section 1.
Figure 6:
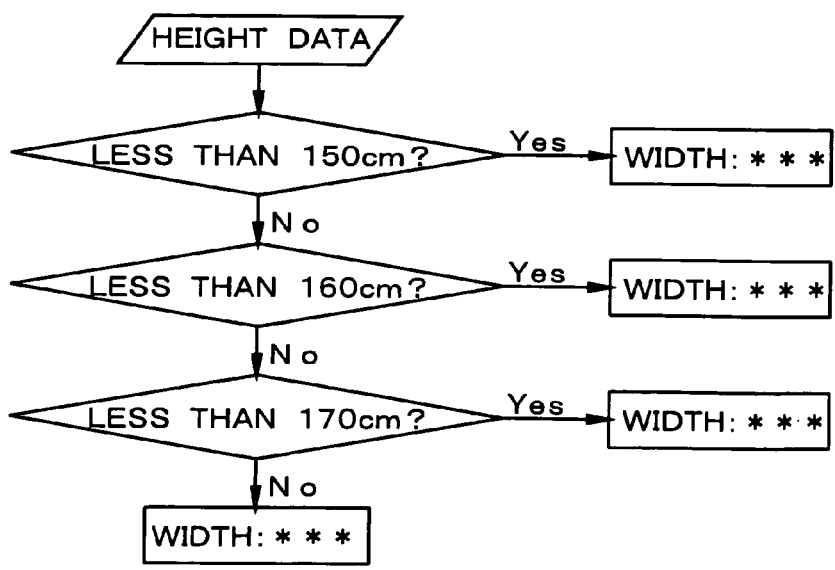
FIG. 6 is a diagram showing an example of the flow of the procedure for setting the side-sitting detection area 6.

Next, a modified example 1 of the present embodiment will be described. In the present modified example, the center-of-gravity position monitored area (side-sitting position detection area) is automatically set by inputting the height of the user. In addition to the function of the controller 5 of the bed apparatus of embodiment 1, a user body information input unit is provided to the controller 5 of the bed apparatus of the present modified example, and the side-sitting detection area 6 indicated by the shaded portion of FIG. 5 is set in the following manner. FIG. 6 is a diagram showing an example of the flow of the procedure for setting the side-sitting detection area 6 in the present modified example. The width from the edge section of the bed section 1 of the side-sitting detection area 6 is defined and stored in advance in the storage unit 22 of the controller 5 for cases in which the height of the user is less than 150 cm, 150 cm or higher and less than 160 cm, 160 cm or higher and less than 170 cm, and 170 cm or higher. When the height information is inputted to the user body information input unit by inputting the height information of the user via a personal computer, the width that corresponds to the inputted height information is computed by the computing unit 21, and the side-sitting detection area 6 is set by reading the information from the storage unit 22. The width of the side-sitting detection area 6 becomes wider as the height is increased, and the width of the side-sitting detection area 6 narrows as the height is reduced.

The bed section 1 may be divided into a plurality of areas, and the side-sitting position detection areas can be set in accordance with the divided areas. The reference center-of-gravity position (X, Y) of the user is stored at the same time as when the reference body weight $W_S$ of the user is stored in the storage unit of the controller 5, and the bed section 1 is divided into four areas, i.e., a head side, a foot side, a right side, and a left side (upper side and lower side in FIG. 5) as points where the reference center of the gravity position (X, Y) of the user is divided. Each of the four divided areas can be selected as a side-sitting position detection area for side-sitting position detection, or as a non-detection area. In the case that a railing is set at the head side of the bed section 1, for example, and an alarm is thereby not required to be generated when the center-of-gravity position exists at the head side of the side-sitting detection area 6, the two areas of the head side are set as non-detection areas of side-sitting position detection, whereby the bed section can be set so that the side-sitting position is not detected even when a center-of-gravity position is present on the head side of the side-sitting detection area 6. In this manner, an area having the width calculated in the manner described above becomes the center-of-gravity position monitoring area for a portion of the detection areas in the divided area. The second determination unit determines that the user is in a side-sitting position when the center-of-gravity position of the user is in the center-of-gravity position monitoring area. The number of divisions of the bed section 1 is not limited to four, and any number of divisions can be set as targets for monitoring the state of a patient. The number of detection areas in the divided areas is also arbitrary. The position of the division points is not limited to the reference center-of-gravity position, and any position can be used.

Modified example 2 of the present embodiment will be described next. In the present modified example, the division positions for setting the width of the center-of-gravity position monitored area (side-sitting position detection area) and the side-sitting position detection area are calculated using a formula. The controller 5 of the bed apparatus of the present modified example is provided with a user body information input unit in the same manner as modified example 1, and the width of the side-sitting detection area 6 and division positions indicated by the shaded portions of FIG. 5 can be set in the following manner. Assuming that the width of the side-sitting detection area 6 is dependent on the length of the thigh, the width of the side-sitting detection area 6 becomes wider as the height increases because it is thought that height is generally greater for people that have a longer thigh, and the width of the side-sitting detection area 6 narrows as the height is reduced. When the height information of the user is inputted using a personal computer, the computing unit 21 of the controller 5 computes the width $|d_1|$ from the edge of the bed section 1 of a suitable side-sitting detection area 6 in relation to the inputted height information by using EQ. 2, for example.

$$|d_1|=aL+C_1 \quad [\text{EQ. 2}]$$

($d_1$: width from the edge of the bed section 1 of the side-sitting detection area 6, a: coefficient of determination, L: height, $C_1$: compensation constant)

The computing unit 21 of the controller 5 computes the division position x of the suitable side-sitting detection area 6 in relation to the inputted height information by using EQ. 3 below. The division position of the side-sitting detection area 6 increases in the plus direction with respect to the X axis as the height increases, and increases in the minus direction as the height is reduced.

$$x=bL+C_2 \quad [\text{EQ. 3}]$$

(x: division position of the side-sitting detection area 6, b: coefficient of determination, L: height, $C_2$: compensation constant)

The division position in the X-axis direction of the side-sitting detection area 6 is determined by EQ. 3, and when, e.g., the division position y in the Y-axis direction is set to be the center of the width of the bed ($y=B_Y/2$) the bed section 1 can be divided into four areas. Each of the four divided areas can be selected to be a detection area for side-sitting position detection or to be a non-detection area in the same manner as modified example 1. An area having the width calculated in the manner described above becomes the center-of-gravity position monitoring area for a portion of the detection areas in the divided area. The second determination unit determines that the user is in a side-sitting position when the center-of-gravity position of the user is in the center-of-gravity position monitoring area.

Figure 7:
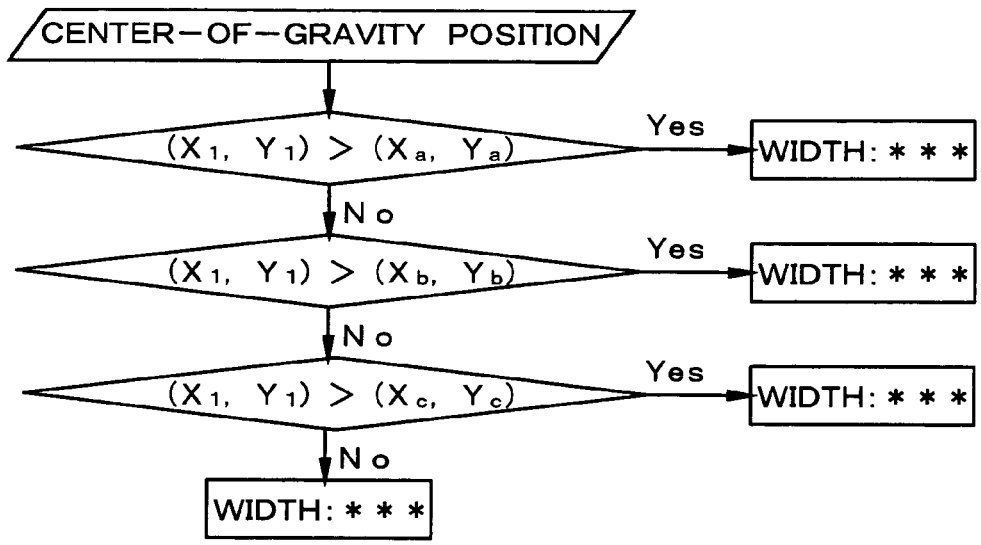
FIG. 7 is a diagram showing an example of the flow of the procedure for setting the side-sitting detection area 6.

Modified example 3 of the present embodiment will be described next. The present modified example is one in which the height of the user is estimated from the computed value of the center-of-gravity position of the user on the bed section 1. In the present modified example, the side-sitting detection area 6 shown in FIG. 5 can be set in the following manner. FIG. 7 is a flowchart of the procedure for setting the side-sitting detection area 6 in the present modified example. The relationship between the height and the center-of-gravity position is defined and stored in advance in the storage unit 22 of the controller 5 (a height of less than 150 cm or the like when the center-of-gravity position $(X_1, Y_1)<(X_a, Y_a)$, for example). The computing unit 21 computes the height of the user on the basis of the center-of-gravity position $(X_1, Y_a)$ of the user at this time when a personal computer is operated or an operating switch of the controller 5 is pressed with the user in a face-up position, for example. The width of the side-sitting detection area 6 and the division position are set by substituting the computed height into the EQS. 2 and 3 above and performing the calculation. The division position for setting the width of the center-of-gravity position monitored area (side-sitting position detection area) and the side-sitting position detection area are thereby obtained, and the bed section 1 can be divided into four areas when, e.g., the division position y in the Y-axis direction is used as the center ($y=B_Y/2$) of the width of the bed in the same manner as modified example 2 described above. Each of the four divided areas can be selected as a side-sitting position detection area for side-sitting position detection or as a non-detection area in the same manner as modified examples 1 and 2. An area having the width calculated in the manner described above becomes the center-of-gravity position monitoring area for a portion of the detection areas in the divided area. The second determination unit determines that the user is in a side-sitting position when the center-of-gravity position of the user is in the center-of-gravity position monitoring area.

Modified example 4 of the present embodiment will be described next. The controller 5 of the bed apparatus of the present modified example is provided with a bed height storage unit and a bed height determination unit, in addition to the function of the controller 5 of the bed apparatus of embodiment 1. When the height H of the bed section 1 is greater than the height at which the feet of the user make contact with the floor in the side-sitting position, there are cases in which the patient's feet do not reach the floor and the value of the body weight $W_T$ of the patient is not reduced even if the patent is in the side-sitting position. In this case, it can be determined that the patient is in the side-sitting position by using only the determination result of the second determination unit in the case that the bed height determination unit has determined that the bed height is equal to or greater than the reference value, even if the first determination unit does not detect a reduction in the body weight.

Figure 8:
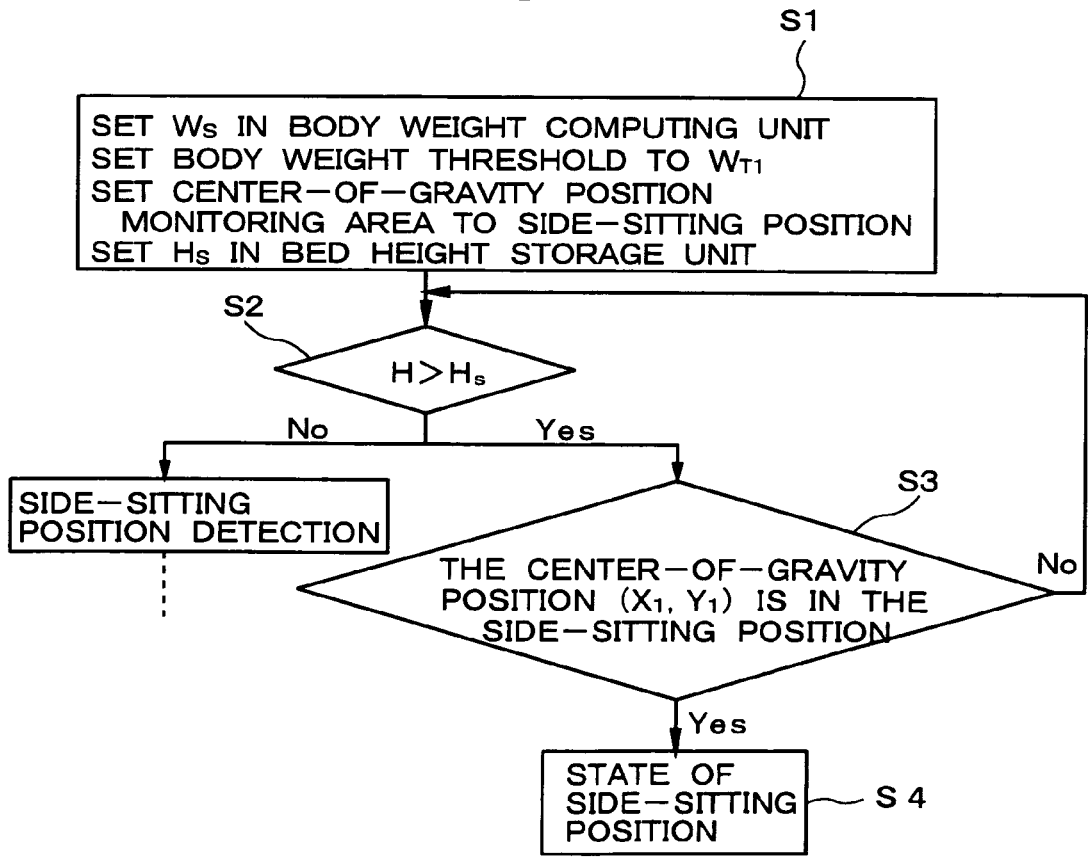
FIG. 8 is a diagram showing the flow of side-sitting detection.

When the bed apparatus provided with a bed-departure prediction and detection system according to the present embodiment is an electric bed, for example, the bed controller can be used to ascertain the bed orientation. The controller 5 and the bed controller are connected and the bed orientation information is transmitted to the controller 5. An operation switch on the controller 5 (not shown) is pressed or a personal computer is operated, whereby the bed section height reference value $H_S$ in which the user's feet are placed on the floor when in a side-sitting position is stored in advance in the bed height storage unit of the controller 5, and when the bed height determination unit has determined that the height H of the bed section 1 is greater than the bed section height reference value $H_S$ (step 2), the side-sitting position state is determined (step 4) by merely determining the center-of-gravity position regardless of the result of the body weight threshold determination (step 3), and an alarm is set so as to be generated in accordance with the result. FIG. 8 is a flowchart of the series of operations described above.

As described above, false alarms can be reduced in relation to the side-sitting position by determining the bed height in addition to side-sitting position detection in embodiment 1 and by determining that the state is a side-sitting position by using only a center-of-gravity position determination when the height H of the bed section 1 is greater than the bed section height reference value $H_S$.

The height H of the bed section 1 and the detection/non-detection areas of the side-sitting position at the height H are stored in advance in the storage unit 22 of the controller 5, whereby the side-sitting position detection area can be switched in accordance with the height H of the bed section 1. A railing is often disposed at least on the head side in order to prevent the user from falling when, e.g., the height H of the bed section 1 is greater than the bed section height reference value $H_S$. Therefore, only the foot side is set and stored in advance in the storage unit 22 of the controller 5 as the side-sitting position detection area when, e.g., the height H of the bed section 1 is greater than the bed section height reference value $H_S$, with consideration given to the convenience of the hospital or facility that uses the apparatus in this manner. In such a configuration, the fact that the center-of-gravity position of the user is present on the head side of the bed section 1 will not be detected as a side-sitting position when the height H of the bed section 1 is greater than the bed section height reference value $H_S$. In this function, the height H of the bed section 1 can be stored in a stepwise fashion in accordance with judgment of a caregiver, and the function can be used to select detection and non-detection of the side-sitting detection area 6 in accordance with the height of each step. Some of the detection areas in the divided area are selected in accordance with the height H of the bed section 1, and these areas are the center-of-gravity position monitoring areas.

The bed apparatus according to embodiment 2 of the present invention will be described next. The present embodiment differs in that the controller 5 has a sit-up detection function rather than a side-sitting position detection function, but the configuration is otherwise the same as in the bed apparatus of embodiment 1. The sit-up detection function detects that the user is in a sit-up state.

The controller 5 of the bed apparatus of the present embodiment has a center-of-gravity movement distance computing unit, a center-of-gravity movement distance threshold setting unit, a center-of-gravity distance time difference setting unit, and a body weight range setting unit, in addition to the function of the controller 5 of the bed apparatus of embodiment 1.

The center-of-gravity position movement distance computing unit calculates the movement distance of the center-of-gravity position from calculation results of the present position of the center of gravity and from the calculation results of the position of the center of gravity at a previous point in time that precedes this time by a center-of-gravity movement distance time difference $T_2$, and this calculation is carried out each time the computing unit 21 of the controller 5 reads a load signal at each fixed interval of time. The movement that occurs when a user sits up is assumed to be a movement from a face-up position to a sitting position with the legs extended, or from a face-up position to a recumbent position, and then to a sitting position with the legs extended. In any of these movements, the center of gravity moves from the head side to the foot side in the length direction (the X-axis direction in FIG. 5). Therefore, consideration is given to the center-of-gravity position movement distance in only the X axis direction during sit-up detection.

The movement distance $|\Delta X|$ of the center-of-gravity position in the X-axis direction can be expressed in EQ. 4 below, wherein $(X_2, Y_2)$ at time $t_2$ is the center-of-gravity position of the user, and $(X_{2-T2}, Y_{2-T2})$ is the center-of-gravity position of the past value $t_{2-T2}$ that precedes time $t_2$ by a center-of-gravity distance time difference $T_2$. According to this equation, the center-of-gravity movement distance computing unit calculates the movement distance of the center-of-gravity position of the user on the bed section 1.

$$|\Delta X| = |X_2 - X_{2-T2}|$$ [EQ. 4]

($T_2$: the movement distance of the center-of-gravity position at the time difference)

The first determination unit monitors a body weight $W_T$ of the user on the bed section 1, which is calculated by the body weight computing unit, determines whether the body weight $W_T$ of the user at time $t_2$ is equal to or less than a first threshold, and determines whether the body weight $W_T$ of the user is within a prescribed range at time $t_2'$-$T_2$ that precedes time $t_2$ by a center-of-gravity distance time difference $T_2$. The second determination unit also monitors the movement distance $|\Delta X|$ of the center-of-gravity position of the user in the X axis direction, and determines whether the movement distance $|\Delta X|$ of the center-of-gravity position of the user on the bed section 1 at time difference $T_2$ exceeds a second threshold.

The body weight threshold setting unit sets a first threshold for the body weight $W_T$ of the user when the user on the bed section 1 is determined to have made a sit-up movement. The body weight range setting unit sets a prescribed range for the body weight $W_T$. The center-of-gravity movement distance threshold setting unit sets a second threshold of the center-of-gravity position movement distance in the sit-up detection. The center-of-gravity movement distance time difference setting unit sets the center-of-gravity movement distance time difference $T_2$. These set values are inputted from a personal computer connected to the controller 5, are calculated in the computing unit of the controller 5, and are stored in a storage unit.

The alarm apparatus generates an alarm in accordance with the determination results of the first determination unit and the second determination unit. The alarm selection unit has a function for selecting the existence of an alarm and the type of alarm. When an alarm is generated, a nurse is notified by way of a nurse call signal 29, or a personal computer 28 or the like, and notification can be made using an alarm display unit 25 of the controller 5.

Figure 9:
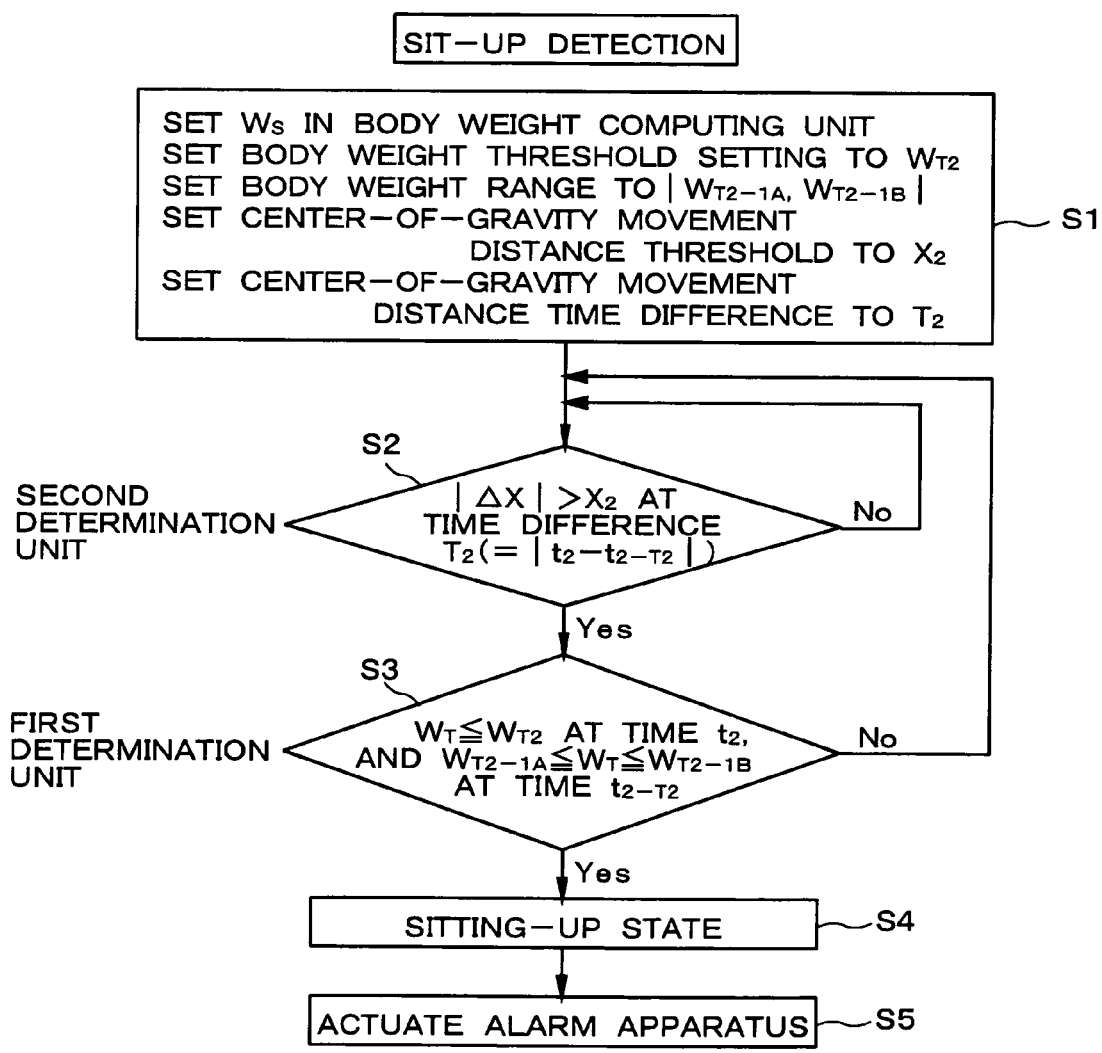
FIG. 9 is a diagram showing the flow from sit-up detection to alarm apparatus actuation.

FIG. 9 shows the flow from sit-up detection until the alarm apparatus is activated. A reference body weight $W_S$ of the user on the bed section 1 is calculated in advance at a reference time by the body weight computing unit of the computing unit 21 of the controller 5, a body weight threshold $W_{T2}$ is set by the body weight threshold setting unit, a prescribed body weight range $|W_{T2-1A}, W_{T2-1B}|$ is set by the body weight range setting unit, a center-of-gravity movement distance threshold $X_2$ is set by the center-of-gravity movement distance threshold setting unit, and a center-of-gravity movement distance time difference $T_2$ is set by the center-of-gravity movement distance time difference setting unit. These values are stored in the storage unit 22 of the controller 5 (step 1).

The center-of-gravity position moves in the X-axis direction when the user has performed a sit-up action. The center-of-gravity position movement distance $|\Delta X|$ of the user is computed based on the calculation results of the current position of the center of gravity, and the calculation results of the position of the center of gravity at a previous point in time that precedes this time by a center-of-gravity movement distance time difference $T_2$ (e.g., 5 seconds), and this calculation is carried out each time the computing unit 21 of the controller 5 reads a load signal at each fixed interval of time. The second determination unit determines (step 2) that the movement distance $|\Delta X|$ of the center-of-gravity position has exceed the center-of-gravity movement distance threshold $X_2$ when ($|\Delta X| > X_2$) the movement distance $|\Delta X|$ (the movement distance in the X-axis direction of the center of gravity at time difference $T_2$ (e.g., 5 seconds)) of the center-of-gravity position computed based on the calculation results of the center-of-gravity position in the X-axis direction of the user at time $t_2$, and the calculation results of the center-of-gravity position computed based on the calculation results of the center-of-gravity position at a previous point in time $t_2$-$T_2$ that precedes time $t_2$ by a center-of-gravity movement distance time difference $T_2$ (e.g., 5 seconds), is greater than the center-of-gravity movement distance threshold $X_2$ ($X_2$=30 cm, for example), which is the second threshold.

However, when only the center-of-gravity position movement distance in the X axis direction is monitored, the movement cannot be determined to be movement of the center of gravity that is caused by an item being placed on the bed section 1 in which the user is lying down, or another non-user person leaning or sitting on the bed section, and there are conceivably cases when these movements may be mistakenly determined to be a sit-up movement. In order to avoid such errors, the first determination unit determines that the movement distance $|\Delta X|$ of the center-of-gravity position in the X axis direction exceeds the second threshold at time difference $T_2$. At the time that the second determination unit makes this determination ($t=t_2$), the first determination unit determines whether the body weight $W_T$ of the user on the bed section 1 is equal to or less than a first threshold ($W_T \leq W_{T2}$; e.g., 125% or less of the reference body weight $W_T$ of the user; in other words, whether the body weight $W_T$ is a load produced by only the body weight of the user), and also determines whether the body weight $W_T$ of the user is within a prescribed range ($W_{T2-1A} \leq W_T \leq W_{T2-1B}$, e.g., 75 to 125% of the reference body weight $W_S$ of the user; in other words, whether the user is present on the bed) during the point in time ($t=t_{2-Ts}$) that precedes $t=t_2$ by a time difference $T_2$ (Step 3).

The user is detected as being in a state of sitting up (step 4) when the second determination unit has determined that the movement distance $|\Delta X|$ of the center-of-gravity position, which is calculated from the calculation results of the center-of-gravity position of the user in the X axis direction at time $t_2$ and from the calculation results of the center-of-gravity position at a point in time $t_{2-T2}$ that precedes time $t_2$ by a center-of-gravity movement distance time difference $T_2$, has exceeded the center-of-gravity movement distance threshold $X_2$, which is a second threshold, and has also determined that the body weight $W_T$ of the user at time $t_2$ is equal to or less than the body weight reference value body weight $W_{T2}$, which is a first threshold, and that the body weight $W_T$ of the user is within a prescribed range ($W_{T2-1A} \leq W_T \leq W_{T2-1B}$) at a point in time $t_{2-T2}$ the precedes time $t_2$ by a center-of-gravity movement distance time difference $T_2$. An alarm can be generated in accordance with the result (step 5).

The alarm apparatus generates an alarm in accordance with the sit-up detection results, and the alarm selection unit has a function for selecting the existence of an alarm and the type of alarm. When an alarm is generated, a nurse is notified by way of a nurse call signal 29, or a personal computer 28 or the like, and notification can be made using an alarm display unit 25 of the controller 5.

As described above, sit-up detection is carried out by determining whether the body weight $W_T$ of the user on the bed section 1 is equal to or less than a body weight threshold when the center-of-gravity position movement distance exceeds a second threshold, and/or determining whether the body weight $W_T$ of the user is within a prescribed range at a point in time that precedes by a time difference $T_2$ the time at which the center-of-gravity position movement distance exceeds a second threshold. As a result, it is possible to determine the movement to be movement of the center-of-gravity position that is caused by an item being placed on the bed section 1 in which the user is lying down, or another non-user person leaning or sitting on the bed section, and errors in the sit-up detection can be reduced. When the center of gravity moves due to the railing or other accessories being removed, and the second threshold determination unit has determined that the movement distance $|\Delta X|$ of the center-of-gravity position of the user at time difference $T_2$ has exceeded the center-of-gravity movement distance threshold $X_2$, which is a second threshold, the first determination unit determines in conjunction therewith whether the body weight Wt of the user is within a prescribed range at the point in time that precedes by a time difference $T_2$ the time at which the center-of-gravity position movement distance has exceeded a second threshold. Therefore, misdetections can be prevented.

Figure 10:
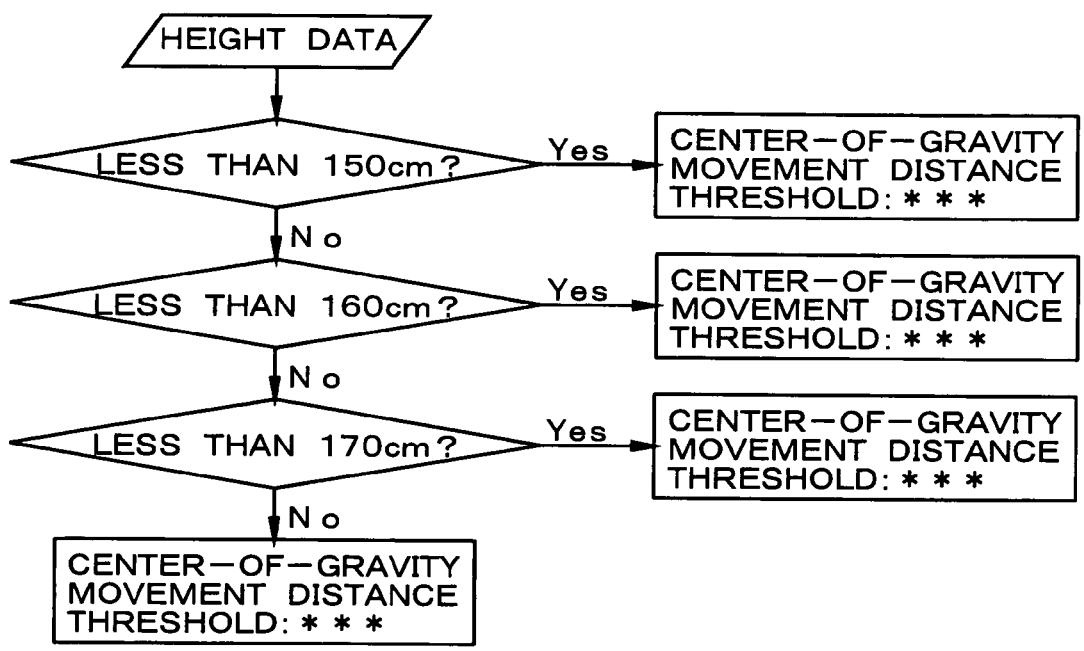
FIG. 10 is a diagram showing an example of the flow of the procedure for setting the center-of-gravity movement distance threshold.

Next, a modified example 1 of the present embodiment will be described. In the present modified example, the center-of-gravity position monitored area is automatically set by inputting the height of the user. In addition to the function of the controller 5 of the bed apparatus of embodiment 2, a user body information input unit is provided to the controller 5 of the bed apparatus of the present modified example, and the center-of-gravity position movement distance threshold is set in the following manner. FIG. 10 shows an example of the flow of the procedure for setting the center-of-gravity position movement distance threshold in the present modified example. The height of the user is defined and stored in advance in the storage unit 22 of the controller 5 for cases in which the height of the user is less than 150 cm, 150 cm or higher and less than 160 cm, 160 cm or higher and less than 170 cm, and 170 cm or higher. When the height information is inputted to the user body information input unit by inputting the height information of the user via a personal computer, the center-of-gravity movement distance threshold that corresponds to the inputted height information is computed by the computing unit 21, and the center-of-gravity position movement distance threshold can be set by reading the information from the storage unit 22. The center-of-gravity position movement distance threshold of a short-statured user is a low value, and the center-of-gravity position movement distance threshold is higher in accordance with the height of the user. The second determination unit determines that a movement is a sit-up movement when the center-of-gravity position movement distance threshold set in this manner has exceeded the movement distance $|\Delta X|$ of the center-of-gravity position of the user at time difference $T_2$.

Modified example 2 of the present embodiment will be described next. In the present modified example, the center-of-gravity position movement distance threshold is calculated using a formula. The controller 5 of the bed apparatus of the present modified example is provided with a user body information input unit in the same manner as modified example 1, and the center-of-gravity position movement distance threshold can be set in the following manner. Assuming that the center-of-gravity movement distance when the user sits up is dependent on the length of the upper body, the center-of-gravity position movement distance threshold $|d_2|$ can be set based on the relationship shown in EQ. 5 below because it is thought that the length of the upper body is generally greater for tall-statured people. The center-of-gravity position movement distance threshold of a short-statured user is a low value, and the center-of-gravity position movement distance threshold increases in accordance with the height of the user. When the height information of the user is inputted using a personal computer, the computing unit 21 of the controller 5 computes a suitable center-of-gravity position movement distance threshold $|d_2|$ in relation to the inputted height information by using EQ. 5, for example.

$$|d_2|=cL+C_3 \quad [EQ. 5]$$

($d_2$: center-of-gravity position movement distance threshold, c: coefficient of determination, L: height, $C_3$: compensation constant)

The second determination unit determines that a sit-up movement has taken place when the center-of-gravity position movement distance threshold that is set in this manner has exceeded the movement distance $|\Delta X|$ of the center-of-gravity position of the user at time difference $T_2$.

The bed apparatus according to embodiment 3 of the present invention will be described next. The present embodiment differs in that the controller 5 has a weight abnormality detection function rather than a side-sitting position detection function, but the configuration is otherwise the same as in the bed apparatus of embodiment 1. The weight abnormality detection function detects that the computed value of the body weight $W_T$ of the user on the bed section 1 is abnormal.

The controller 5 of the bed apparatus of the present embodiment has a body weight range setting unit, a body weight monitoring unit, and a body weight monitoring time setting unit in addition to the function of the controller 5 of the bed apparatus of embodiment 1.

The zero point compensation function of the controller 5 may be performed, and railings or other accessory items may be removed or added after the reference body weight $W_S$ of the user has been stored, whereby it is possible that the state of the user cannot be correctly monitored when there is a deviation between the body weight $W_T$ of the user on the bed section 1 and the stored reference body weight $W_S$ of the user. Therefore, the abnormality detection unit determines that the computed value of the body weight is outside of a prescribed range (e.g., ±25% of the reference body weight $W_S$ of the user) and detects an abnormality when the body weight $W_T$ of the user on the bed section 1 is outside of the prescribed range. The body weight monitoring unit monitors the time in which the computed value of the body weight has been outside of the prescribed range, and detects whether a prescribed length of time has elapsed (e.g., 20 minutes), whereupon a weight abnormality is detected.

The alarm apparatus generates an alarm in accordance with the result of the weight abnormality detection. The alarm selection unit has a function for selecting the existence of an alarm and the type of alarm. When an alarm is generated, a nurse is notified by way of a nurse call signal 29, or a personal computer 28 or the like, and notification can be made using an alarm display unit 25 of the controller 5.

The body weight range detection unit sets a prescribed range of the body weight $W_T$ of a user on the bed section 1. The body weight monitoring time setting unit sets a prescribed time in which the body weight monitoring unit monitors the time in which the computed value of the body weight is outside of the prescribed range. These settings are inputted from a personal computer connected to the controller 5, computed in the computing unit of the controller 5, and stored in the storage unit.

Figure 11:
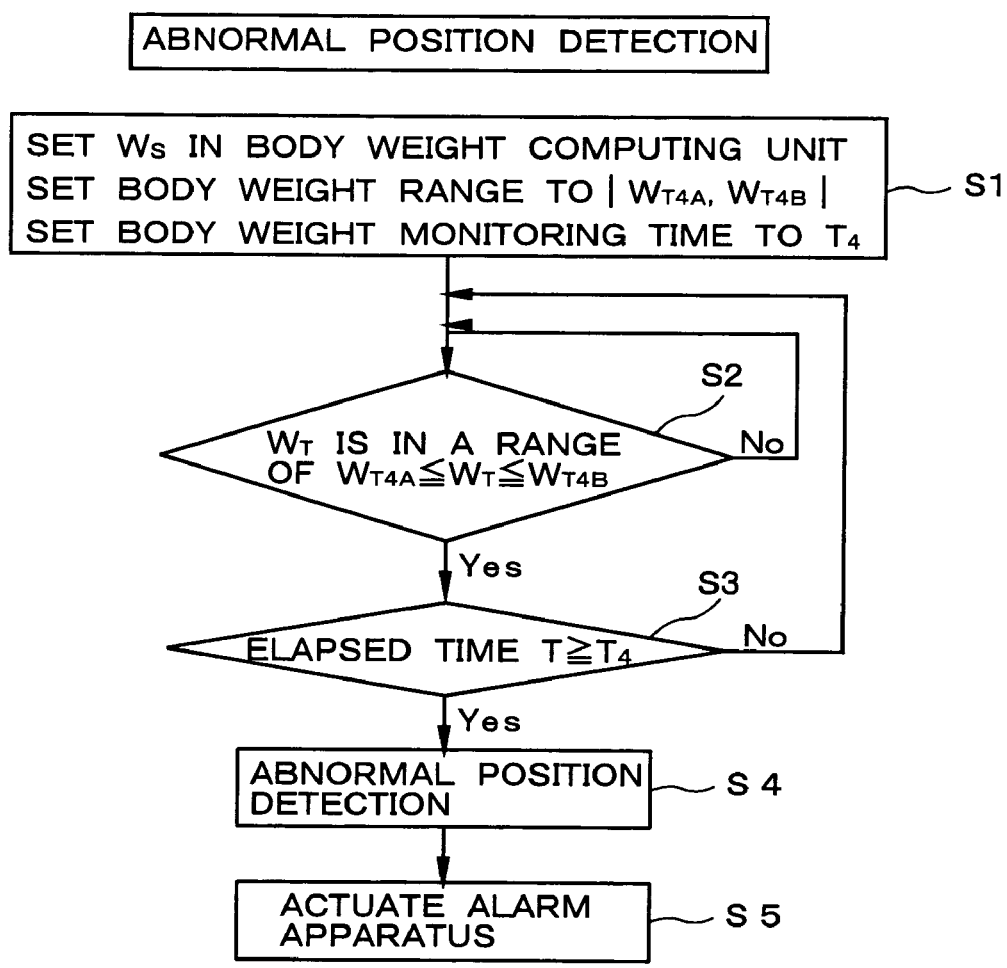
FIG. 11 is a diagram showing the flow from abnormal weight detection to alarm apparatus actuation.

FIG. 11 shows the flow from abnormal weight detection to alarm apparatus actuation. The reference body weight $W_S$ of the user on the bed section 1 is calculated by the body weight computing unit of the computing unit 21 of the controller 5, a prescribed body weight range $|W_{T4A}, W_{T4B}|$ of the user is set by the body weight range setting unit, and a body weight monitoring time $T_4$ for monitoring the body weight $W_T$ of the user is set by the body weight monitoring time setting unit. These values are stored in the storage unit 22 of the controller 5 (step 1).

The body weight monitoring unit monitors the body weight $W_T$ of the user on the bed section 1 computed by the body weight computing unit, and when the body weight $W_T$ of the user is outside of a prescribed range ($W_{T4A} \leq W_T \leq W_{T4B}$), the abnormality detection unit determines that the computed value of the body weight is outside of the prescribed range and detects an abnormality (step 2).

The body weight monitoring unit monitors the time in which the computed value of the body weight is outside the prescribed range, and when this state has continued for a prescribed length of time or longer, the body weight monitoring unit detects (step 3) that the state in which computed value of the body weight is outside the prescribed range has continued for a prescribed length of time or longer ($T \geq T_4$).

The abnormality detection unit determines that the computed value of the body weight is outside of the prescribed range ($W_{T4A} \leq W_T \leq W_{T4B}$) and detects an abnormality, and when the body weight monitoring unit monitors the time in which the computed value of the body weight is outside of the prescribed range and detects that [such a state] has continued for a prescribed length of time or longer ($T \geq T_4$), a weight abnormality on the bed section 1 is detected (step 4). The alarm apparatus may be actuation at this time (step 5).

The alarm apparatus generates an alarm in accordance with the weight abnormality detection function result. The alarm selection unit has a function for selecting the existence of an alarm and the type of alarm. When an alarm is generated, a nurse is notified by way of a nurse call signal 29, or a personal computer 28 or the like, and notification can be made using an alarm display unit 25 of the controller 5.

As described above, the abnormality detection unit determines that the body weight $W_T$ of the user on the bed section 1 is outside of the prescribed range and detects an abnormality during weight abnormality detection, and when the body weight monitoring unit monitors the time in which the computed value of the body weight $W_T$ of the user on the bed section 1 is outside of the prescribed range and detects that such a state has continued for a prescribed length of time or longer, a weight abnormality on the bed section 1 is detected, whereby the body weight $W_T$ of the user on the bed section 1 is monitored.

The bed apparatus according to embodiment 4 of the present invention will be described next. The present embodiment differs in that the controller 5 has an abnormal position detection function rather than a side-sitting position detection function, but the configuration is otherwise the same as in the bed apparatus of embodiment 1. The abnormal position detection function detects that the user on the bed section 1 is, e.g., leaning on the railing (not shown) or on the wall 4, or is otherwise remaining in an unnatural state.

The controller 5 of the bed apparatus of the present embodiment has a body weight center-of-gravity position monitoring unit and a body weight center-of-gravity position monitoring time setting unit in addition to the function of the controller 5 of the bed apparatus of embodiment 1.

In the present embodiment, an abnormal position area is set separately from the side-sitting detection area 6 described in embodiment 1 of the present invention. This area is one in which an abnormality of the user is suspected to be due to a state that is different from a sleeping orientation under normal circumstances and in which a prescribed length of time or longer has elapsed. The area used for detecting this abnormal position may be arbitrarily set by the center-of-gravity position monitored area setting unit in the same manner as the side-sitting detection area 6 described above.

Possible states in which the user may be in an abnormal position on the bed section 1 is a state in which the body of the user is on the bed section 1, and a state in which only a part of the body of the user is on the bed section 1. In order to eliminate the latter state, the value of the body weight $W_T$ of the user is also monitored, whereby an abnormal position can be detected with greater accuracy.

The first determination unit monitors the body weight $W_T$ of a user on the bed section 1 that has been computed by the body weight computing unit, and determines whether the body weight of the user is equal to or greater than a prescribed body weight threshold $W_{T5}$. The second determination unit monitors the center-of-gravity position $(X_5, Y_5)$ of the user and determines whether the center-of-gravity position of the user $(X_5, Y_5)$ is in the center-of-gravity position monitored area of the bed section 1. An abnormal position is detected and an alarm is generated when the first determination unit determines that the body weight of the user is equal to or greater than a prescribed body weight threshold $W_{T5}$, the body weight center-of-gravity position monitoring unit monitors the state in which the second determination unit is determining that the center-of-gravity position ($X_5, Y_5$) of the user is in the center-of-gravity position monitored area of the bed section 1, and this state has continued for a prescribed length of time (the body weight center-of-gravity position monitoring time, e.g., 10 minutes) that has been set by the body weight center-of-gravity position monitoring time setting unit.

The alarm apparatus generates an alarm in accordance with the abnormal position detection result. The alarm selection unit has a function for selecting the existence of an alarm and the type of alarm. When an alarm is generated, a nurse is notified by way of a nurse call signal 29, or a personal computer 28 or the like, and notification can be made using an alarm display unit 25 of the controller 5.

The body weight threshold setting unit sets the body weight threshold of the body weight $W_T$ of when it is determined that the user on the bed section 1 is in an abnormal position. The body weight center-of-gravity monitoring time setting unit sets the prescribed time for monitoring whether the body weight center-of-gravity monitoring unit has determined that the body weight $W_T$ of the user is equal to or greater than a prescribed threshold, and for monitoring the time in which the center of gravity of the user is in a monitored area. These settings are inputted from a personal computer connected to the controller 5, computed in the computing unit of the controller 5, and stored in the storage unit.

Figure 12:
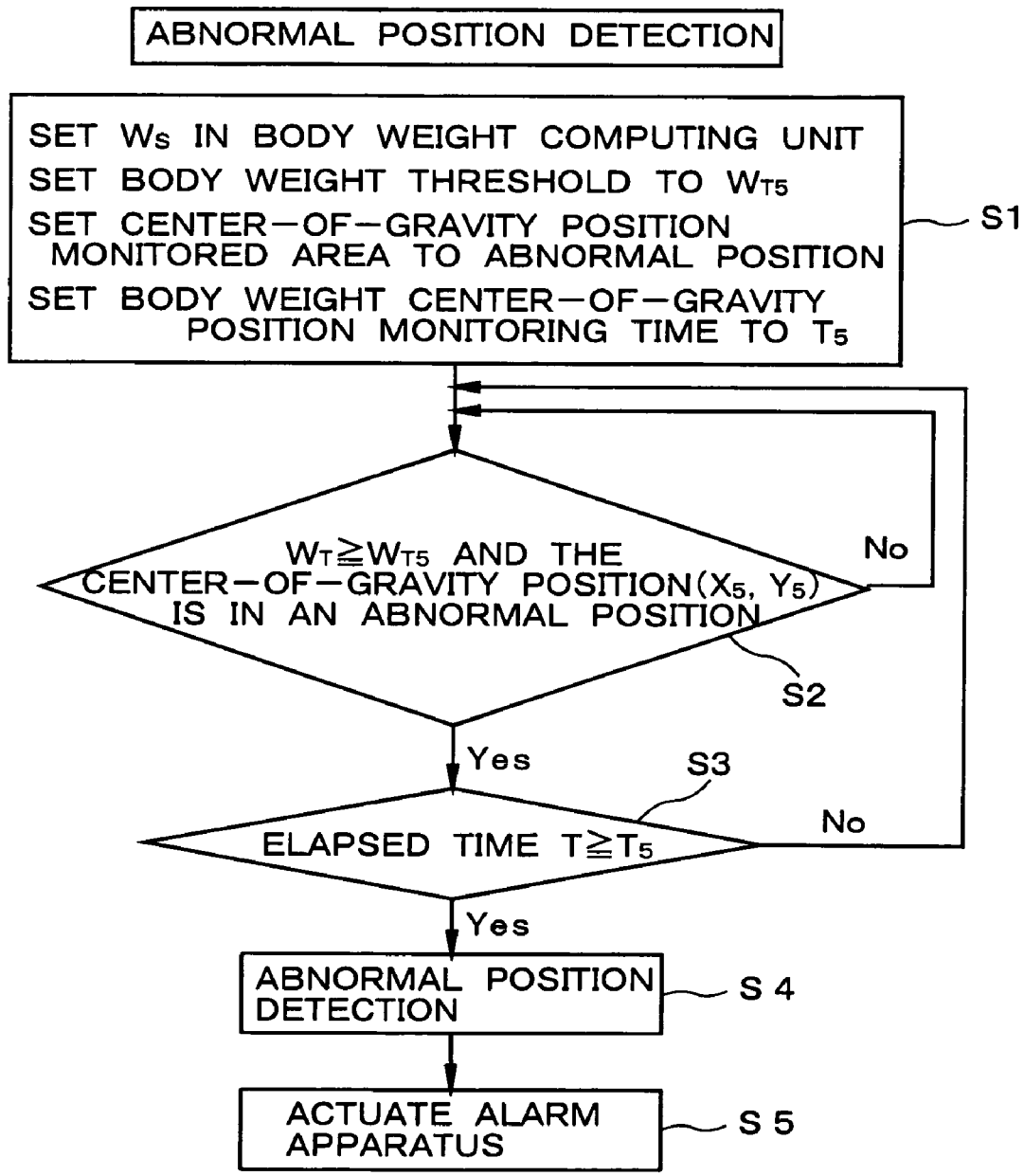
FIG. 12 is a diagram showing the flow from abnormal position detection to alarm apparatus actuation.

FIG. 12 shows the flow from abnormal position detection to alarm apparatus actuation. The reference body weight $W_S$ of the user on the bed section 1 is computed by the body weight computing unit of the computing unit 21 of the controller 5 in advance when a reference is obtained; the body weight threshold $W_{T5}$ is set by the body weight threshold setting unit, the abnormal position is set by the abnormal position setting unit; the body weight center-of-gravity monitoring time $T_5$, which is used to monitor whether the body weight $W_T$ of the user is equal to or greater than the body weight threshold $W_{T5}$ and to monitor the time in which center-of-gravity position of the user is in the abnormal position, is set by the body weight center-of-gravity monitoring time setting unit; and these values are stored in the storage unit 22 of the controller 5 (step 1).

When the body weight $W_T$ of the user on the bed section 1 computed by the body weight computing unit is equal to or greater than a prescribed body weight threshold $W_{T5}$ (e.g., 50% of the reference body weight $W_S$ of the user), the first determination unit determines that the body weight $W_T$ of the user is equal to or greater than a body weight threshold $W_{T5}$; and when the center-of-gravity position ($X_5$, $Y_5$) is in the abnormal position of the bed section 1, the second determination unit determines that the center-of-gravity position of the user is in an abnormal position (step 2). When the body weight center-of-gravity position monitoring unit detects (step S3) that the body weight $W_T$ of the user is equal to or greater than the body weight threshold $W_{T5}$ and that a state in which the center-of-gravity position is in a abnormal position has continued for a prescribed length of time or longer ($T \geq T_5$), the user is detected to be in an abnormal position (step 4). The alarm apparatus may be actuation at this time (step 5).

As described above, when the center of gravity of the user is determined to be in an abnormal position during abnormal position detection, the value of the body weight $W_T$ of the user is also monitored, and when it has been detected that the body weight $W_T$ of the user is equal to or greater than the body weight threshold and that the state in which the center-of-gravity position is in an abnormal position has continued for a prescribed length of time or longer, the user is detected to be in an abnormal position. Abnormal position detection can thereby be performed with greater accuracy.

The bed apparatus according to embodiment 5 of the present invention will be described next. The bed apparatus of the present embodiment differs in that the apparatus has the detection function of embodiments 1 to 4 described above and at least one alarm apparatus; the body weight values and the body weight thresholds in embodiments 1 to 4 that correspond to the body weights are defined and stored in advance in the storage unit 22 of the controller 5; and the alarm apparatus has a body weight threshold setting unit for setting the body weight threshold by reading the preset body weight thresholds of the detection function in relation to the computed value of the reference body weight $W_S$ of the user. The configuration is otherwise the same as in the bed apparatus of embodiment 1. The bed apparatus of the present embodiment may also actuate an alarm apparatus in accordance with the result of each determination.

Figure 13:
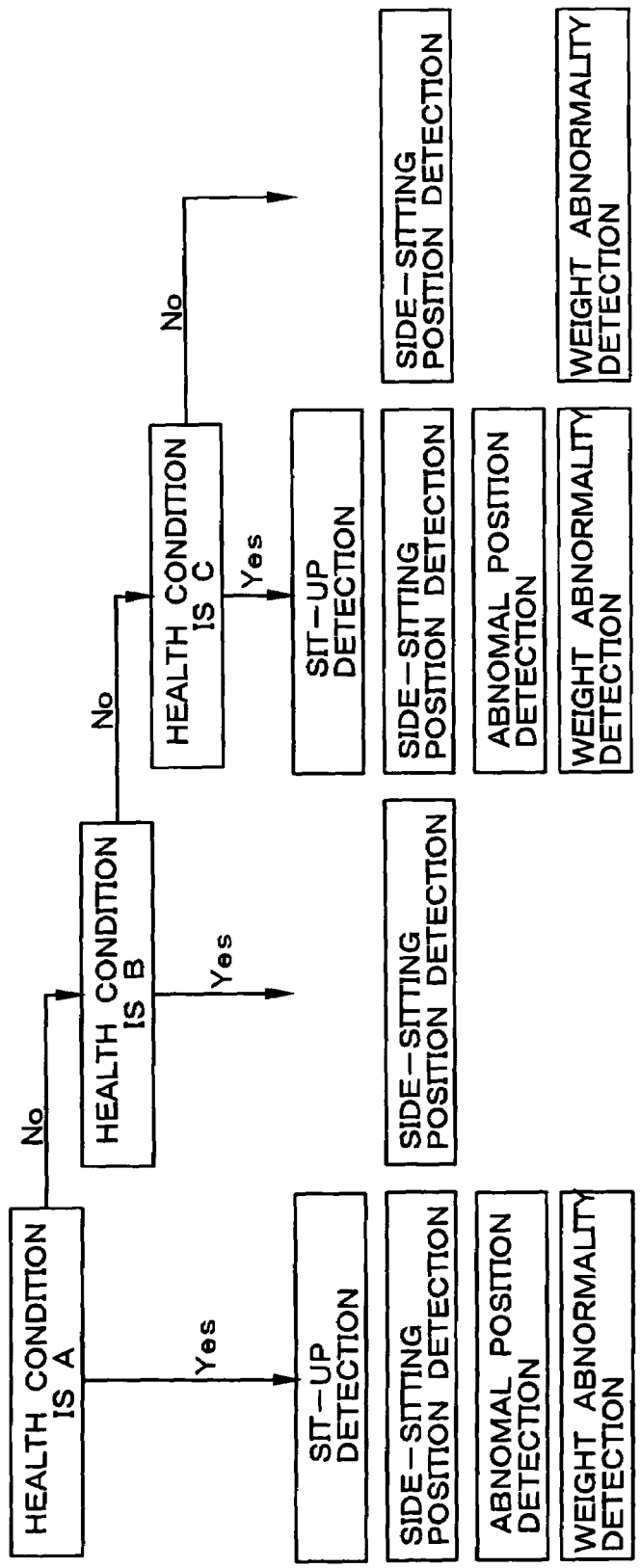
FIG. 13 is a diagram showing an example of the flow of alarm selection in which a recommended detection item is selected when responses are made via a personal computer to questions about the health condition of a user.

The bed apparatus according to embodiment 6 of the present invention will be described next. The bed apparatus of the present embodiment is provided with all of the detection functions of embodiments 1 to 4 described above, but differs in that the apparatus has a body information input unit for inputting the body information of the user; an alarm setting unit that can select the presence or absence of an alarm is to be generated and select an optimal alarm unit based on the inputted body information of the user; and a related-threshold setting unit that can set a threshold related to the alarm setting unit. The configuration is otherwise the same. The bed apparatus of the present embodiment can select whether an alarm is generated when a side-sitting position, a sit-up action, a weight abnormality, or an abnormal position is detected, with dependence on the health condition of the user. The controller 5 may be provided with a function that can selected the alarm items, and these alarm items can also be selected by operation from a personal computer. It is also possible to provide an operating switch (not shown) of the controller 5 with a function for stopping all of the alarm items. A function in which the recommended alarm items are selected by personal computer operation in response to questions about the health condition of the user may also be provided in the manner shown in FIG. 13.

In embodiments 1 through 6 above, the thresholds, prescribed ranges, side-sitting positions, and the like are inputted using a personal computer connected to the controller 5, and these parameters are calculated by the computing unit 21 of the controller 5. However, the calculations may also be made by the personal computer, and the calculation results can be inputted to the controller 5 from the personal computer.

INDUSTRIAL APPLICABILITY

The present invention is useful in predicting bed-departure and determining the bed-departure and bed-presence of a person that requires nursing care.

The invention claimed is:

1. A bed apparatus, comprising:
a load measuring unit for detecting a load of a bed section and generating a load signal;
a body weight computing unit for computing a body weight of a user positioned on the bed section on a basis of said load signal, said body weight computing unit setting a reference body weight of the user after the user has initially lain on the bed;
a first determination unit for determining whether said body weight is equal to or less than a prescribed threshold, said prescribed threshold being derived from the reference body weight, considering the body weight when the user is sitting on the bed and when the user's feet are placed on the floor;

a center-of-gravity position computing unit for computing a center-of-gravity position of said user on the basis of said load signal;

a second determination unit for determining whether said center-of-gravity position is in a monitored area of the bed section, said monitored area comprising an edge sitting position at an edge of the bed section;

a body weight threshold setting means for setting the prescribed threshold of said body weight, and a center-of-gravity position monitored area setting unit for setting said monitored area of said center-of-gravity position; and a controller for detecting whether said user is sitting at said edge sitting position of the bed section, based on a combination of when said first determination unit has determined that said body weight is equal to or less than the prescribed threshold and that said second determination unit has determined that said center-of-gravity position is within said monitored area, wherein said user is detected as sitting at said edge sitting position of the bed section, when said first determination unit has determined that said body weight is equal to or less than a prescribed threshold in combination with said second determination unit that has determined that said center-of-gravity position is within said monitored area.

2. The bed apparatus according to claim 1, further comprising an alarm unit for generating an alarm when the state of said user has been detected.

3. The bed apparatus according to claim 1, further comprising:
    a bed height storage unit for storing a bed section height reference value; and
    a bed height determination unit for determining whether a current bed section height is greater than the bed section height reference value,
    wherein the state of said user is detected solely by a determination result of said second determination unit regardless of a determination result of said first determination unit when said bed height determination unit has determined that the current bed section height is greater than the bed section height reference value.

4. The bed apparatus according to claim 1, further comprising a user body information input unit for inputting body information of the user, and
    wherein said center-of-gravity position monitored area setting unit sets an optimal center-of-gravity position monitored area, based on the inputted user body information.

5. The bed apparatus according to claim 1, wherein said center-of-gravity position monitored area setting unit sets an optimal center-of-gravity position monitored area, based on said center-of-gravity position of the user computed by said center-of-gravity position computing unit.

6. The bed apparatus according to claim 1, wherein said center of gravity position comprises a side-sitting position of the user where the user is sitting at an edge of the bed.

7. The bed apparatus according to claim 4, wherein said body information of the user comprises a height information of the user, and
    wherein said optimal center-of-gravity position monitored area is based on said height information to adjust a width of the edge sitting position.

* * * * *